(12) United States Patent
Varella E Silva

(10) Patent No.: US 10,078,025 B2
(45) Date of Patent: Sep. 18, 2018

(54) DEVICE FOR DETERMINING TENSION ON ANCHORING LINES

(71) Applicant: Jairo Bastos De Araújo, Resende (BR)

(72) Inventor: Fausto Roberto Varella E Silva, Rio de Janeiro (BR)

(73) Assignee: BASTOS DE ARAÚJO, JAIRO, Resende (BR)

( * ) Notice: Subject to any disclaimer, the term of this patent is extended or adjusted under 35 U.S.C. 154(b) by 0 days.

(21) Appl. No.: 15/126,753

(22) PCT Filed: Mar. 26, 2014

(86) PCT No.: PCT/BR2014/000097
§ 371 (c)(1),
(2) Date: Sep. 16, 2016

(87) PCT Pub. No.: WO2015/157830
PCT Pub. Date: Oct. 22, 2015

(65) Prior Publication Data
US 2017/0089781 A1    Mar. 30, 2017

(51) Int. Cl.
| G01L 5/08 | (2006.01) |
| F16G 15/00 | (2006.01) |
| F16G 15/08 | (2006.01) |
| G01N 3/06 | (2006.01) |
| G01N 19/00 | (2006.01) |

(52) U.S. Cl.
CPC .............. *G01L 5/08* (2013.01); *F16G 15/00* (2013.01); *F16G 15/08* (2013.01); *G01N 3/064* (2013.01); *G01N 19/00* (2013.01)

(58) Field of Classification Search
CPC ........................................................ G01L 5/08
See application file for complete search history.

(56) References Cited

U.S. PATENT DOCUMENTS

| 4,078,407 A | * | 3/1978 | Ditges | B21L 15/00 |
| | | | | 72/18.9 |
| 4,977,783 A | * | 12/1990 | Pratt | B66C 13/16 |
| | | | | 73/862.392 |
| 5,845,893 A | * | 12/1998 | Groves | B63B 21/10 |
| | | | | 114/293 |

(Continued)

FOREIGN PATENT DOCUMENTS

| GB | 532772 A | 1/1941 |
| GB | 2042743 A | 9/1980 |
| GB | 2183350 A | 6/1986 |

OTHER PUBLICATIONS

International Search Report from international Appl. No. PCT/BR2014/00009, dated Nov. 11, 2014.

*Primary Examiner* — Paul West
*Assistant Examiner* — Mark A Shabman
(74) *Attorney, Agent, or Firm* — Nevrivy Patent Law Group P.L.L.C.

(57) ABSTRACT

It is reported in the present invention a device (A) to monitor the tension on an anchoring line (LA) of a floating platform for oil exploration or production at sea, which is mounted at a point on the anchoring line without it becoming an integral part thereof, which basically comprises: an upper bar (1) and a lower bar (2), which are interconnected at one end by a hydraulic cylinder (CH1) and on the other end by a solid vertical bar (4).

4 Claims, 5 Drawing Sheets

(56) References Cited

U.S. PATENT DOCUMENTS

| | | | | |
|---|---|---|---|---|
| 7,313,975 B1* | 1/2008 | Scorteanu | ............... | G01L 5/103 |
| | | | | 254/257 |
| 7,418,875 B2* | 9/2008 | Kohno | ................... | G01L 5/102 |
| | | | | 198/502.3 |
| 8,171,715 B2* | 5/2012 | Segura | ...................... | B66C 1/10 |
| | | | | 59/78 |
| 2003/0155564 A1* | 8/2003 | Fontenot | ................ | B63B 21/04 |
| | | | | 254/358 |
| 2013/0067881 A1* | 3/2013 | Khrakovsky | ........... | F16G 15/06 |
| | | | | 59/86 |
| 2016/0023720 A1* | 1/2016 | Dugas | .................... | B63B 21/18 |
| | | | | 114/200 |

\* cited by examiner

DEVICE FOR DETERMINING TENSION ON ANCHORING LINES

FIELD OF THE INVENTION

The present invention is related to devices and methods for determining the tension of several anchoring lines whose function is to maintain stabilized at a certain position, platforms or floating units which are prospecting and producing oil at sea. More particularly to a device that is independent of the anchoring line, i.e., not an integral part thereof. More specifically, to a device which employs a monitoring system in real time.

BACKGROUND OF THE INVENTION

The oil production on an offshore environment, with increasing water depths, has become a real challenge in order to stabilize through mooring lines, the platforms or the floating units securely in operating position.

This is due not only by its own weight that these mooring lines reach due to the depth, also by all the drag influences they are exposed to because of sea currents, sometimes in different directions according to the depth, as well as by their own swing due by the waves on the sea surface and by the drag by winds acting on the floating unit.

The factors mentioned above as an example, together with the platform operational problems and also by the mooring manufacturing, may cause the breaking of the anchoring lines.

The disruption of one or more anchoring lines can lead the floating unit to a shift in position to beyond the safety margin and can cause very serious problems, particularly relating to the production pipeline connected to it, which may break leading to major environmental disasters as well as risk of death to the crew members.

The main guarantee of the integrity of the entire anchoring system, which maintains a given floating unit in a safe operation, is based on monitoring the tensile force wherein each of the anchoring lines are subjected to.

When they are being constructing, the platforms have as the integrated device, monitoring systems in order to monitor the anchoring lines that will eventually be linked to them. These integrated systems are subjected to the marine environment action which, over time, begin to provide mechanical and electrical failures and start to compromise the security as a whole. It is almost mandatory to use alternative device such that the monitoring of the stress tension in these mooring lines is performed.

It is very old the concern about the integrity of vessels anchoring lines, even with those simpler even with those that doesn't have a greater commitment than that of only to keep the vessel positioned.

The document GB 532 772 A of 1941 is a good example of this type of concern and means of prevention. This document discloses a link-shaped device that becomes part of an anchoring line, constructed with a central element sectioned. Electric contacts are fixed in each end of the sectioned central section of this element, being spaced from one another. These contacts are connected to a module which is laterally fixed to the link and houses batteries and a lamp. When the tension is excessive, the trend is that the chain link suffers an elongation deformation, and the two branches of the central element become in contact closing the electric circuit that lights the lamp and draws the attention of the involved personnel.

Over time the techniques has evolved to a more sophisticated devices, based on calculations made with data derived from correlations with phenomena suffered by a mooring line, for example, the existence of a relationship between the frequency of vibration of a certain line and the active tension force. In this technique, the device measure the natural frequency of a line vibration and the line tension may be calculated using the line specific weight and its free length between two points of support or attachment.

The document PI 0401668-8 A illustrates another tension monitoring mode or the disruption in submerged lines, and in general, among them, the anchoring lines. It comprises a device fixed to a region of a particular line with a sensor that is related to a parameter indicating a variation in the position of this device, and a communication unit for transmitting to a control base a variation that has occurred in said parameter. This method is positional and based on the fact that an anchoring line assume a certain inclination relating to the water line, and its angle is a function of the active tensile force acting on the line. The acting tension are obtained by calculations based on the measurement of the angles that are recorded by the sensor.

Another type of device for this purpose is shown in US 2013/0067881 A1 which shows an assembly of a device similar to the shackle, with a body in which one side is in the form of a fixed pin with arms extending in parallel in each end of this fixed pin. On the other ends of each one arms is interposed a pin. In at least one arm, a recess is formed inside which is housed a pressure sensor which acts as tensile meter.

Other examples are based on technical data of deformation or reduction in the width of a given link and on the changing of the steel electromagnetic properties when it is tensioned.

What is important to note is that some of the solutions presented above are permanently installed or are integrating part of the anchoring lines system, which are used as a component thereof. The technique lacks from a device for monitoring the tension in an anchoring line that is simple in its design, and which is adapted at one point of an anchoring line without being an integral part thereof, and thus, once collected the necessary data, the machine can be dismantled from this line and be mounted on another line, resulting in reduced costs.

SUMMARY OF THE INVENTION

It is object of the invention a device to measure and monitor the tension acting on the anchoring lines of any floating platform that operates at the oil exploration and production activities at sea or other ambient with water.

The device is mounted at a point onto an anchoring line without it becomes as an integral part thereof, such that, once collected the necessary data, this device is dismantled from the first line and is mounted on another line in which it is necessary a tension measurement without any special maneuver.

The objective is achieved by designing this device which comprises basically: an upper bar and a lower horizontal bar, which are interconnected at one end by a hydraulic cylinder and at the other end by a solid vertical bar, optionally with an extensometer adapted in this vertical bar and, in another possibility, the solid vertical bar is replaced by a second hydraulic cylinder.

DETAILED DESCRIPTION OF THE INVENTION

The present invention is relating to a device for measuring and/or to monitor the tension forces acting on an anchoring line at any floating platform that operates in exploration and oil production activities at sea, device which is mounted at a point on that anchoring line without becomes an integral part thereof. Once collected the necessary data, this device can be removed from the first line and mounted on another line in which it is necessary a tension measurement.

The anchoring line (LA) mentioned throughout this report is formed by a plurality of links (W).

Figure 1:
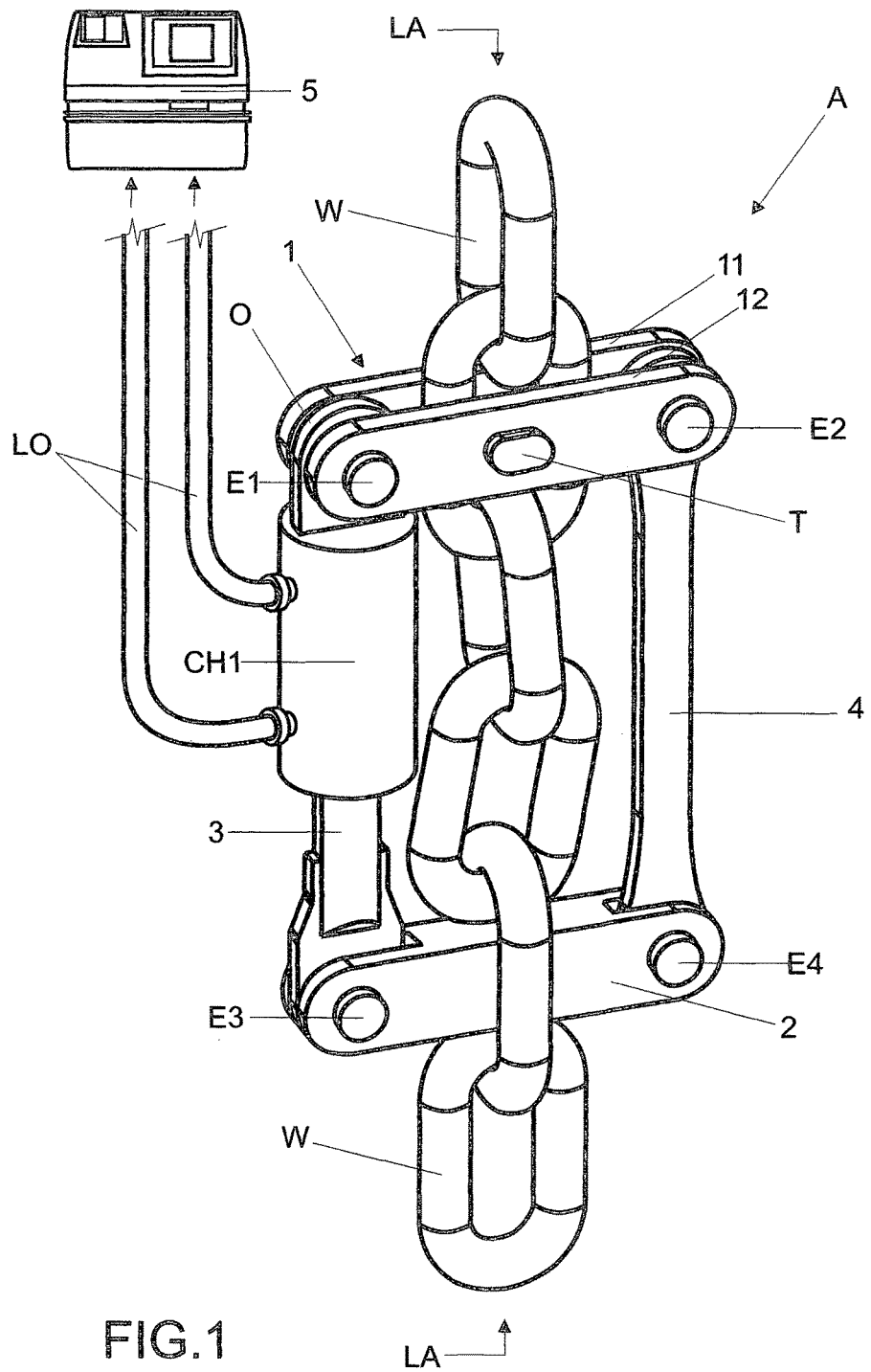
FIG. 1 is a perspective representation of the present invention device in operation, attached to an anchoring line.
Figure 2:
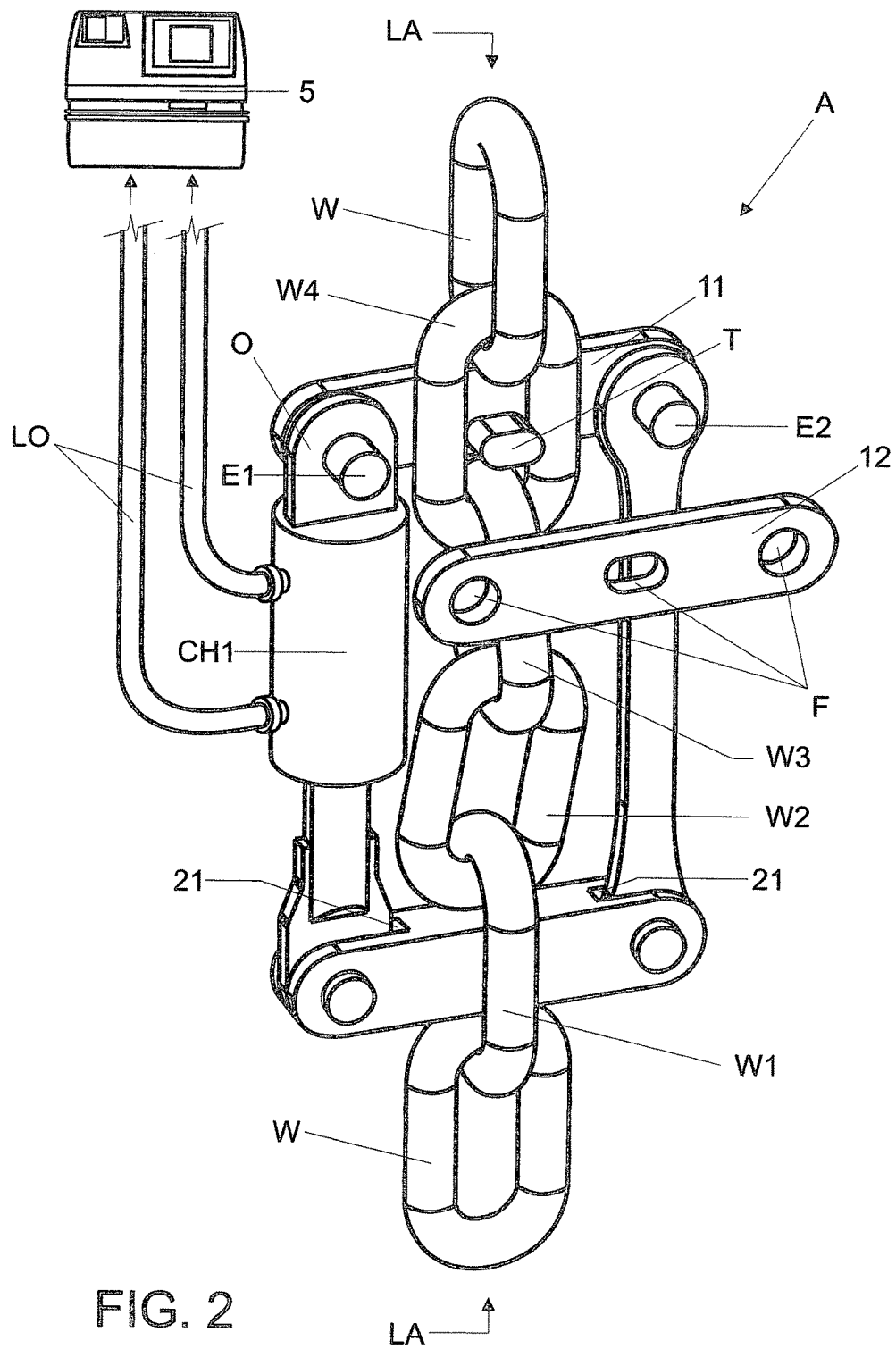
FIG. 2 is a perspective representation of the present invention device in operation, attached to an anchoring line and with the upper horizontal bar dismantled.
Figure 3:
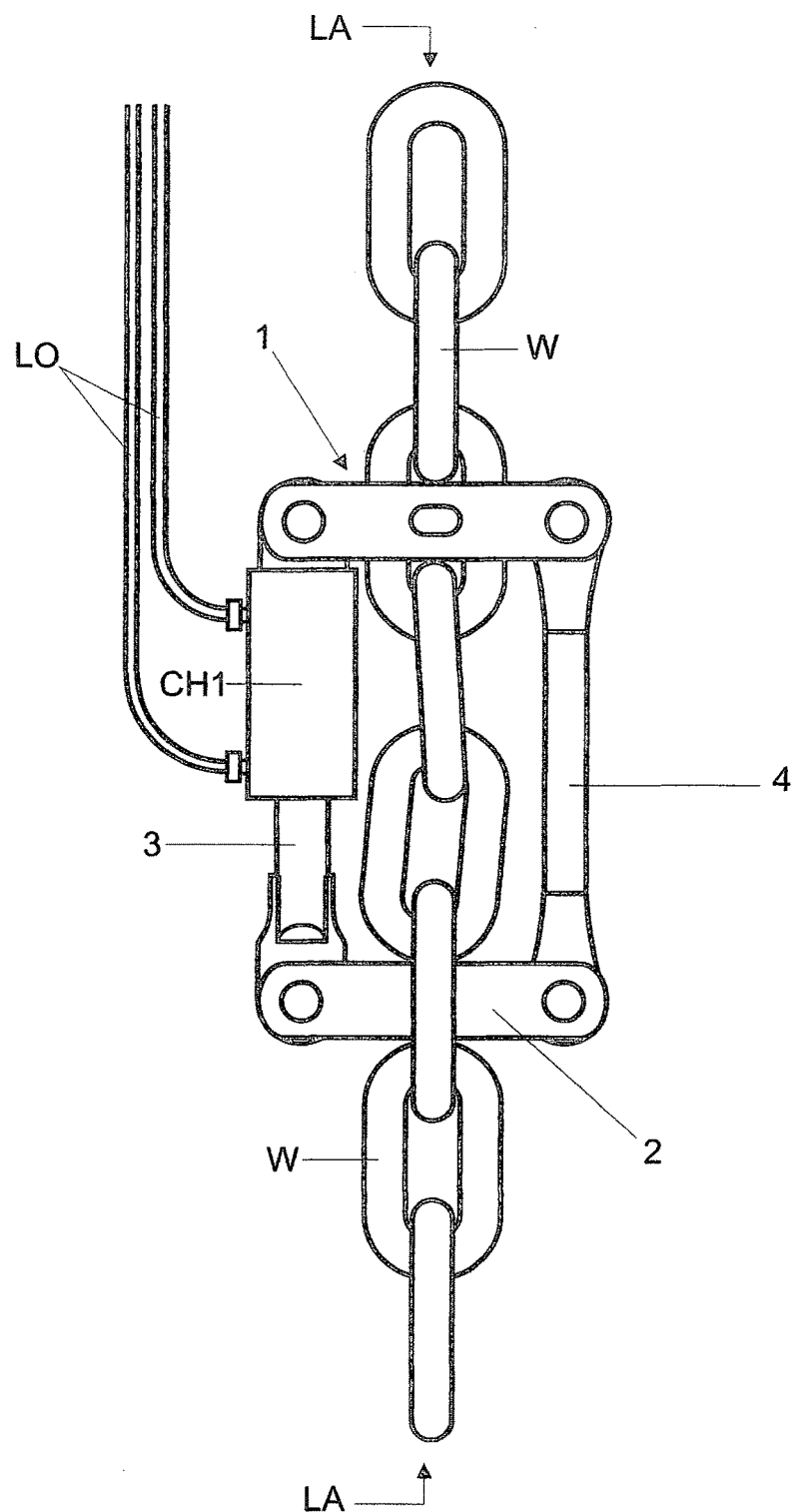
FIG. 3 is a representation in front view of the device showed in FIG. 1.
Figure 4:
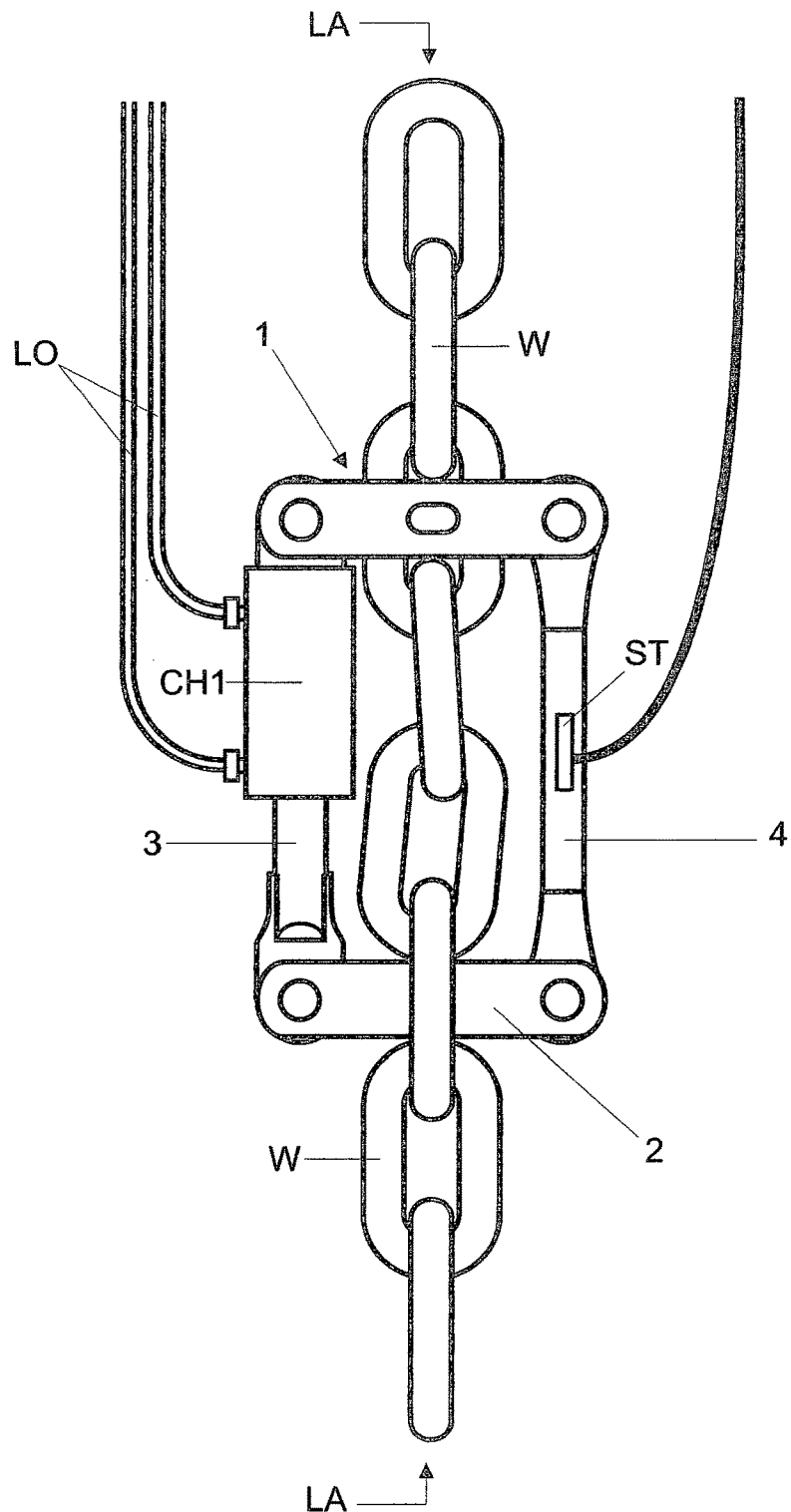
FIG. 4 is a representation in front view of the device showed in FIG. 1 improved with an extensometer fitted on the vertical bar.
Figure 5:
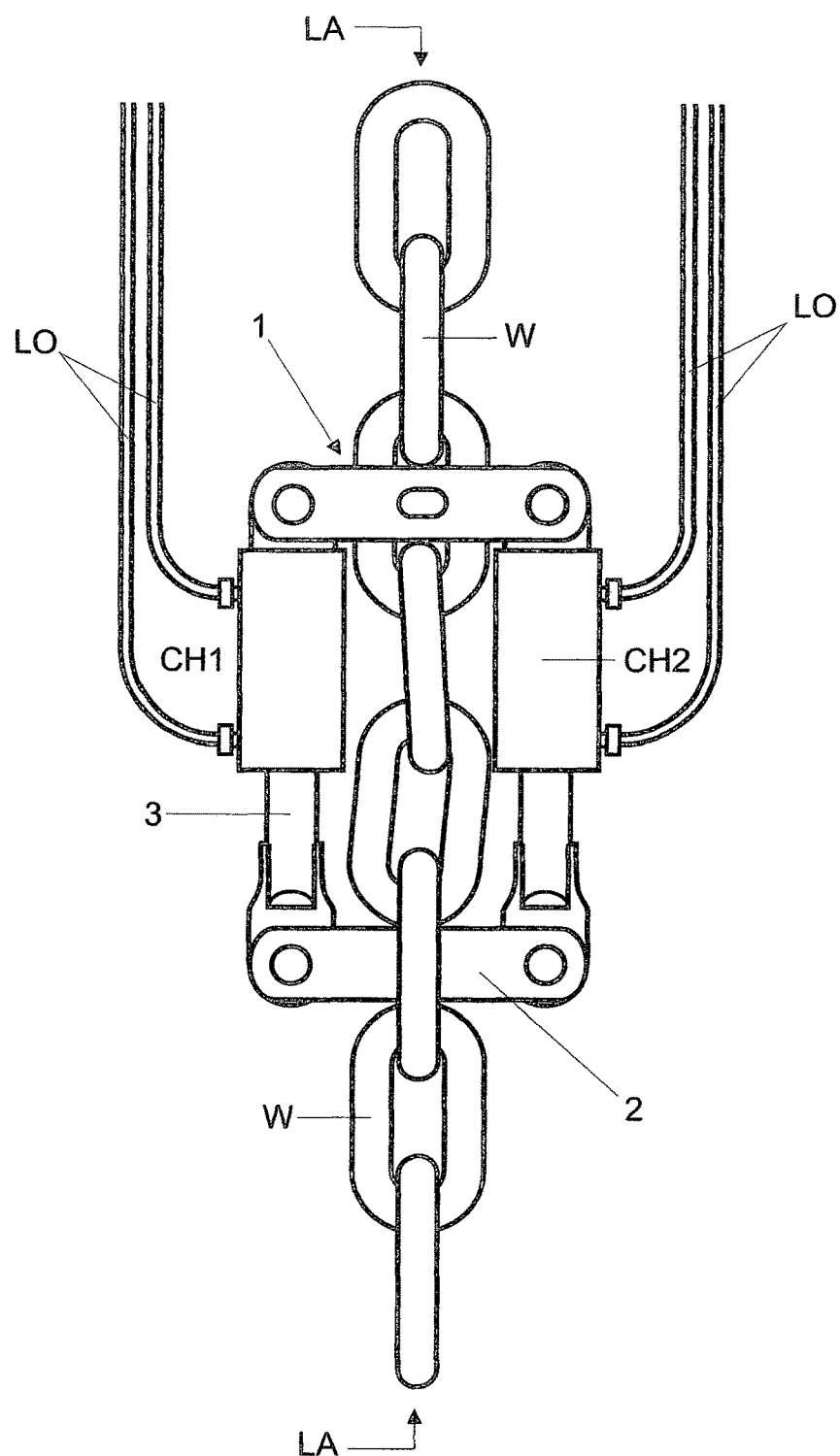
FIG. 5 is a representation in front view of the device showed in FIG. 1 improved with the single vertical bar replaced by a second hydraulic cylinder.

The device (A) to monitor the tension in an anchoring line can be seen at the FIGS. 1, 2 and 3 and comprises:

- an upper bar (1), comprising a first plate (11) which has rigidly connected near each of its ends: a first pin (E1) and a second pin (E2) and, in its central region, an anti-slip lock pin (T); and a second plate (12) (FIG. 2, dismantled) which, in the same regions of the pins (E1, E2) and of the lock pin (T), has holes (F) such that these elements can be fixed, serving so as the first tension supporting point, acting on the portion between the anchoring line (LA) and the floating platform (not shown in the figures);
- a solid lower bar (2), (FIGS. 1, 2, 3, 4 and 5) which presents indentations (21) near their ends with holes (F) in which are fixed a third pin (E3) and a fourth pin (E4), serving so as the second tension supporting point acting on the portion between the anchoring line (LA) and the seabed;
- a hydraulic cylinder (CH1) (FIGS. 1, 2, 3, 4 and 5) which is linked by a pad eye plate (O) integrated in its body to the first pin (E1) of the upper bar (1), and by the end of its rod (3) to the third pin (E3) of the lower bar (2), and has also the function that, when retracts its rod (3) by the hydraulic power unit (5) and, by reading a calibrated hydraulic pressure, record the tension force acting on the anchoring line (LA) when it is acting as a momentum transmission element between the horizontal bars (1 and 2).
- a vertical bar (4) with length slightly lower than the hydraulic cylinder (CH1) side with its rod (3) extended, connected by its ends to the second pin (E2) of the upper bar (1) and to the fourth pin (E4) of the lower bar (2), which serves as a reacting element to the momentum transmitted by the hydraulic cylinder (CH1) by be trapped between these horizontal bars (1 and 2);

The said vertical bar (4) can be selected from the following configurations:
- a solid vertical bar (4), (FIG. 3);
- a solid vertical bar (4) with an extensometer (ST) connected to it and electrically connected to the floating platform (FIG. 4); and
- a second hydraulic cylinder (CH2) (FIG. 5);

- a hydraulic power unit (5) (FIG. 1 and FIG. 2) is responsible for providing, maintaining and reading the hydraulic pressure which feeds the hydraulic cylinders (CH1, CH2), which are connected to it by oil supply lines (LO), whereas the extensometer signals (ST) are monitored by a panel on the hydraulic power unit (5).

The mounting of the device (A), best seen in FIG. 2, involves the occupation of at least four links chain (W) of an anchoring line (LA), which are parallel to the hydraulic cylinder (CH1) and the vertical bar (4), where a first link chain (W1) is crossed by the lower bar (2), a second link chain (W2) and a third link chain (W3), both of them free above the first link chain (W1), and a fourth link chain (W4), where there are attached the first and the second profiles (11, 12) and the lock pin (T), which runs through one link chain (W4) and prevents the sliding of the upper bar (1).

On applying the hydraulic pressure to the first cylinder (CH1) by the hydraulic power unit (5), the piston rod (3) retracts causing the side of the hydraulic cylinder (CH1) to become as the same length than that of the vertical bar (4), the second link (W2) and the third link (W3) slacken, and the tension force acting on the anchoring is transferred to the device (A).

On operating the device (A) when the hydraulic power unit (5) is working to maintain the hydraulic cylinder rod (3) retracted, the upper bar (1) and the lower bar (2) are parallel to each other. When mounting or dismounting, there is a small angle between the upper bar (1) and the lower bar (2) due to the hydraulic cylinder rod (3) be distended.

The tension measurement transferred from the anchoring line (LA) to the device (A) may be chosen from:
- reading the hydraulic pressure from the first hydraulic cylinder (CH1) on the hydraulic power unit (5), and the pressure measurement is converted to a tension measurement;
- reading the hydraulic pressure from the first hydraulic cylinder (CH1) on the hydraulic power unit (5), and reading on the hydraulic power unit (5) the signal from the extensometer (ST) installed on the vertical bar (4); and
- reading the hydraulic pressures from the first hydraulic cylinder (CH1) and from the second hydraulic cylinder (CH2) on the hydraulic power unit (5), whereby the pressure measurements are converted to a tension measure.

According to the features that were exposed above, it can be safely stated that the device (A) to measure and/or monitoring the tension in an anchoring line (LA) has as its main advantages:

a) it is not necessary to disconnect or handling the anchoring line (LA) in order to get the tension measure;

b) get immediately the tension measure;

c) detect immediately the breaking of an anchoring line (LA);

d) operates in an environment dry or submerged in water;

e) may be maintained permanently mounted to an anchoring line (LA), and is only triggered when it is desired to obtain the tension value on the line, or be removed from a particular line and mounted on another so as to measure the tension effort in all the anchoring lines (LA) of the floating platform;

f) has a simple and flexible operation, and does not interfere with the floating platform operation.

While the invention has been described in its preferred embodiment, the main concept guiding the present invention is a device to monitor the tension on an anchoring line of a floating platform for oil exploration and production at sea, said device being mounted on a point on the anchoring line without becoming an integral part thereof, so that, once collected the necessary data, this device can be dismounted from the first line and be mounted in another line in which it is necessary to make a measurement tension, without any special maneuver, maintaining itself preserved about its innovative character, where those usually skilled in the art may discern and practice variations, modifications, alterations, adaptations and appropriate and compatible equivalents to the concerning working environment without, however, departing from the comprehensiveness of the spirit and scope of the invention that are represented by the claims that follow.

The invention claimed is:

1. A device for determining tension on anchoring lines, characterized in that comprises:
   an upper bar (1), comprising a first plate (11) which has rigidly connected near each of its ends: a first pin (E1) and a second pin (E2) and, in its central region, an anti-slip lock (T); and a second plate (12) which, in the same regions of the pins (E1, E2) and of the lock (T), has holes (F) so that the pins and the lock can be fixed, serving as a first tension supporting point, acting on a portion between the anchoring line (LA) and a floating platform;
   a solid lower bar (2) which comprises a first and second indentation (21) near a periphery of the lower bar with holes (F) in which are fixed a third pin (E3) and a fourth pin (E4), serving as a second tension supporting point acting on a portion between the anchoring line (LA) and a seabed;
   a hydraulic cylinder (CH1) which is linked by a pad eye plate (O) integrated in its body to the first pin (E1) of the upper bar (1), and by an end of the hydraulic cylinder rod (3) to the third pin (E3) of the lower bar (2), and has also the function that, when activated, retracts its rod (3) and, by reading a calibrated hydraulic pressure, recording the tension force acting on the anchoring line (LA) while it is acting as a momentum transmission element between the horizontal bars (1 and 2);
   a vertical bar (4) with length lower than that of the hydraulic cylinder (CH1), connected by its ends to the second pin (E2) of the upper bar (1) and to the fourth pin (E4) of the lower bar (2), which serves as a reacting element to the momentum transmitted by the hydraulic cylinder (CH1) by being positioned between these horizontal bars (1 and 2);
   the said vertical bar (4) comprising a configuration selected from the group consisting of:
   i) a solid vertical bar (4);
   ii) a solid vertical bar (4) with an extensometer (ST) connected to it and electrically connected to the floating platform, wherein extensometer signals (ST) are monitored by a panel on the floating platform; and
   iii) a second hydraulic cylinder (CH2);
   a hydraulic power unit (5) located on the floating platform is responsible for providing, maintaining and reading the hydraulic pressure which feeds the one or more hydraulic cylinders (CH1, CH2), which are connected to it by oil supply lines (LO).

2. The device according to claim 1, wherein the device is mounted on an anchoring line, wherein the device (A) spans at least four links (W) of the anchoring line (LA), which are parallel to the hydraulic cylinder (CH1) and the vertical bar (4), wherein a first link (W1) is crossed by the lower bar (2), a second link (W2) and a third link (W3), both of them free above the first link (W1), and a fourth link (W4), where there are attached the first and the second plates (11, 12) and the lock (T), which runs through the interior of the fourth link (W4) and prevents the sliding of the upper bar (1).

3. The device according to claim 1, characterized in that on applying the hydraulic pressure to the first cylinder (CH1), the piston rod (3) retracts causing the side of the hydraulic cylinder (CH1) to become the same length as the vertical bar (4), the second link (W2) and the third link (W3) slacken, and the tension force acting on the anchoring line is transferred to the device (A).

4. The device according to claim 1, characterized in that the tension measurement transferred from the anchoring line (LA) to the device (A) is selected from the group consisting of:
   reading the hydraulic pressure in the first hydraulic cylinder (CH1), which is calibrated, and the pressure measurement is converted to a tension measurement;
   reading the hydraulic pressure in the first hydraulic cylinder (CH1), and the further reading by an extensometer (ST) installed on the vertical bar (4); and
   reading the hydraulic pressure in the first hydraulic cylinder (CH1) and reading of a hydraulic pressure in the second hydraulic cylinder (CH2), both of them calibrated, whereby the pressure measurements are converted to a tension measurement.

* * * * *